United States Patent [19]

Slusarchyk et al.

[11] 3,941,779

[45] Mar. 2, 1976

[54] METHOD FOR PRODUCING 2-(SUBSTITUTED THIO)-3-CEPHEM DERIVATIVES

[75] Inventors: William A. Slusarchyk, Belle Mead; Joseph Edward Dolfini, Princeton; Marian G. Young, Kendall Park, all of N.J.

[73] Assignee: E. R. Squibb & Sons, Inc., Princeton, N.J.

[22] Filed: Nov. 12, 1973

[21] Appl. No.: 415,198

[52] U.S. Cl............................ 260/243 C; 424/246
[51] Int. Cl.².............. C07D 501/04; C07D 501/22
[58] Field of Search............................... 260/243 C

[56] References Cited
UNITED STATES PATENTS
3,660,395   5/1972   Wright et al.................... 260/243 C

*Primary Examiner*—Paul M. Coughlan, Jr.
*Attorney, Agent, or Firm*—Lawrence S. Levinson; Merle J. Smith

[57] ABSTRACT

Treatment of a 7-imido-3-cephem carboxylic acid ester with a thiolating agent in the presence of a strong base yields a 4-(substituted thio)-2-cephem derivative which can be made to rearrange by use of a strong acid to obtain a 2-substituted thio-2-cephem derivative which has antimicrobial activity.

20 Claims, No Drawings

METHOD FOR PRODUCING 2-(SUBSTITUTED THIO)-3-CEPHEM DERIVATIVES

SUMMARY OF THE INVENTION

This invention relates to a new process for the production of a 2-(substituted thio)-2-cephem derivative which has the formula (I)

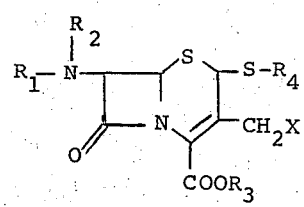

The meaning of the symbols is described below.

The new process comprises treating a 7-imido-3-cephem carboxylic acid ester of the formula (II)

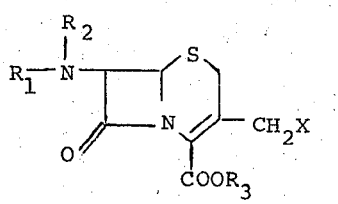

with a thiolating agent in the presence of a strong base to yield a 4-(substituted thio)-7-imido-2-cephem-4-carboxylic acid ester of the formula (III)

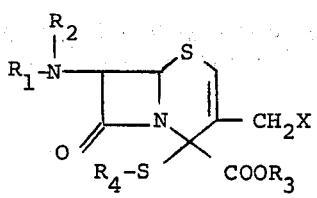

Treatment of the intermediate of formula III with a strong acid or metal salt causes rearrangement to occur and the product obtained is a 7-imido-2-(substituted thio)-3-cephem-4-carboxylic acid ester of the formula (IV)

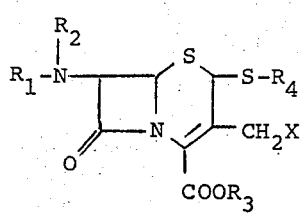

When the protective ester group $R_3$ is removed or displaced, e.g., by acid hydrolysis, a member of a group of known, antimicrobial substances is obtained.

Alternatively, the $R_1$, $R_2$ imide grouping may be cleaved to give a compound of the formula (V)

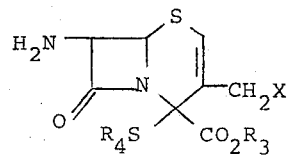

This may be made to react with an acylating agent as known in the art to introduce the radical

to provide the new intermediate of the formula (VI)

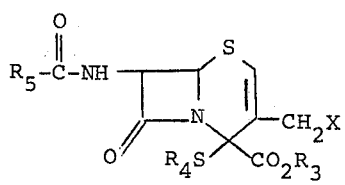

This can then be rearranged with acid or metal salt to give a compound of the formula (VII)

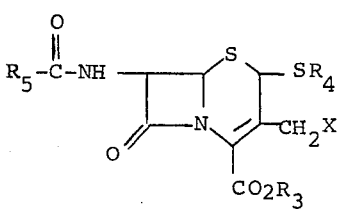

Removal of the $R_3$ group gives a highly active antimicrobial product. Alternatively, the compound of formula V can be rearranged with acid or metal salt to obtain a compound of formula IV wherein $R_1$ and $R_2$ each is hydrogen.

DETAILED DESCRIPTION OF THE INVENTION

The large group of compounds frequently referred to broadly as the cephalosporins are of considerable interest because of their antimicrobial activity. The various members of this group are complex, and simple reactions often cannot be utilized to synthesize them or to obtain them in good yield. Therefore considerable effort must be extended to devise methods for obtaining such complex entities. The method of this invention is a procedure which gives rise to certain useful antibacterial members of the class.

This invention relates to an improved process for obtaining members of a group of known antimicrobial agents of formula IV above.

In the formulas above, and throughout this specification, the symbols have the following meanings.

$R_1$ and $R_2$ each is lower alkanoyl or benzoyl, each of which may be substituted with halo, lower alkyl or lower alkoxy, or taken together with the nitrogen form an alkyl 1,2-dicarboxylic acid of up to 8 carbons, which may be fused into an aromatic ring, e.g., maleimide, succinimide, phthalimide or naphthalene 1,2-dicarboxylic acid imide. Phthalimide is preferred. In the particular instance of formula IV in connection with the alternate method referred to above, $R_1$ and $R_2$ can be hydrogen.

$R_3$ forms a protecting ester group, e.g., $R_3$ is a lower alkyl group such as t-butyl, a lower alkoxybenzyl group such as p-methoxybenzyl, a halo-lower alkyl group such as 2,2,2-trichloroethyl or a lower alkyl silyl group such as trimethylsilyl. Each of the named groups constitutes a preferred embodiment, especially the t-butyl group. When the protecting group is removed, $R_3$ is hydrogen.

$R_4$ is lower alkyl, substituted lower alkyl wherein the substituent is halo, or lower alkoxy, phenyl or substituted phenyl wherein the phenyl substituent is halo, lower alkoxy, nitro, cyano or carboalkoxy.

X is hydrogen or acetoxy.

The lower alkyl groups referred to above are the one to seven carbon straight or branced chain hydrocarbon groups like methyl, ethyl, propyl, isopropyl, butyl, isobutyl, t-butyl and the like. The first four members and especially the first two are preferred. The lower alkoxy, lower alkylthio and carboalkoxy groups are composed of similar radicals.

The four common halogens are included in the term "halo", but chlorine and bromine are preferred.

The first step of the new process comprises thiolating a compound of formula II in the presence of a strong base. The thiolating agent can be any of a varied group of known agents introducing a substituted sulfur substituent including sulfenyl derivatives or disulfides of the formulas $R_4SY$ or $(R_4S)_2$ respectively. $R_4$ has the meaning defined above and Y is a halogen, preferably chlorine or bromine, or a sulfonic acid ester e.g., $-SO_2-Z$, wherein Z is lower alkyl, phenyl or substituted phenyl; lower alkoxycarbonylthio, e.g., methoxycarbonylthio, lower alkylthio, e.g., methyl thio, etc. About one equivalent or more of the thiolating agent is used.

The reaction is carried out in the presence of a strong base, preferably organometallic bases, especially of the alkali metals. These include alkali metal lower alkoxides like potassium t-butoxide, sodium methoxide or lithium methoxide, lithium aryls like triphenylmethyl lithium, lithium alkylamides like lithium diisopropylamide, lithium cyclohexyl isopropylamide or alkali metal hydrides like sodium hydride. About one equivalent of the strong base (based on starting material) should be present.

The starting material, thiolating agent and strong base are preferably caused to react in a solvent which does not interfere with the reaction. Various inert organic solvents which serve this purpose include for example, dimethoxyethane, dioxane, tetrahydrofuran, dimethylformamide, dimethylsulfoxide, benzene, ether as well as other well known organic solvents and reaction media. Temperatures range from −78° to +30°C. The preferred range is normally −30° to +30°C. The reaction is best conducted under an inert atmosphere, e.g., argon or nitrogen.

The rearrangement of the product of the thiolation reaction described above, i.e., the product of formula III is effected by the use of a strong, preferably anhydrous, acid. Such strong acids include halogenated fatty acids such as trifluoroacetic acid, hydrohalic acids such as hydrochloric acid, arylsulfonic acids such as benzene- or toluenesulfonic acid. The rearrangement can also be effected by means of a mercury ($Hg^{++}$), silver ($Ag^+$) or copper ($Cu^{++}$) salt, e.g., mercuric acetate, which is preferred, silver acetate, cupric acetate or the like. About 0.1 to 1 proportions of acid (based on starting material) are used. About one equivalent of metal salt (based on starting material) is used. The reaction medium is preferably an inert organic solvent such as nitromethane, dimethoxyethane, dioxane, chloroform, methylene chloride or the like. Trifluoroacetic acid is the preferred strong acid since it can, in addition, serve as the reaction medium and also remove the protective ester group $R_3$, when the protective ester group $R_3$ is an acid sensitive group such as t-butyl, p-methoxybenzyl, benzhydryl or the like, during the rearrangement thereby obtaining a product of formula I wherein $R_3$ is hydrogen. Otherwise this is accomplished, for example when $R_3$ is a group such as trichloroethyl by using zinc dust in cold 95% acetic acid.

Since a number of the members of the antibacterial cephalosporin class contain an acyl radical on the 7-amino group, (see for example, U.S. Pat. Nos. 3,720,669 and 3,741,962 in connection with $R_1$ for illustration of such radicals), a particularly preferred embodiment of this invention leads to products having the desired acyl groups. According to this preferred embodiment, a product of formula III is formed as described above. In this case, the phthalamido group is the

radical of choice although the other groups referred to may be used. At this point, the

is selectively cleaved with hydrazine to form a 7-amino-4-(substituted thio)-2-cephem-4-carboxylic acid ester of formula V. Hydrazine itself or hydrate thereof is used; about 1.0 to 1.5 equivalent (based on starting material) is used.

The compound of the formula V is acylated by treatment with an acid halide of the formula $R_5-CO-Y$ or acid anhydride $(R_5CO)_2$, or activated derivative thereof, by conventional procedures (as in the above cited patents) to obtain a product of formula VI. Y is a halogen, preferably chlorine or bromine, azide, p-nitrophenyl, ethoxycarboxyl, etc., and $R_5$ is one of the conventional groups making up the known acyl amino radicals in the 7-position (as in the patents cited above). $R_5$ thus includes lower alkyl, phenyl, phenyl-lower alkyl, e.g., benzyl, phenethyl, α-aminophenyl-lower alkyl, e.g., α-aminobenzyl, phenoxy-lower alkyl, e.g., phenoxymethyl, lower alkoxy, methyl e.g., methoxy, methyl ethoxy, methyl propoxy, methyl lower alkylthio, methyl e.g., methylthio, methyl ethylthio, methyl pyridyl-lower alkyl, e.g., pyridylmethyl, thenyl, furylmethyl, oxazolylmethyl, isoxazolylmethyl, β-lower alkoxy-lower alkenyl, cyclo-lower alkyl-lower alkyl wherein the cyclo-lower alkyl group has 4 to 6 carbons, preferably 5 or 6, e.g., cyclopentylmethyl, cyclohexylethyl, α-amino cyclo-lower alkadiene-lower alkyl, e.g., α-amino cyclohexadienylmethyl, α-amino cyclopentadienylmethyl. The cyclic phenyl, thienyl, pyridyl, furyl, oxazolyl, isoxazolyl, cycloalkyl and cycloalkadienyl groups can also be substituted with one or two lower alkyl, lower alkoxy, halo, nitro, amino or trifluoromethyl groups.

The acylated product of formula VI is then subjected to the rearrangement procedure previously described to obtain a product of the formula

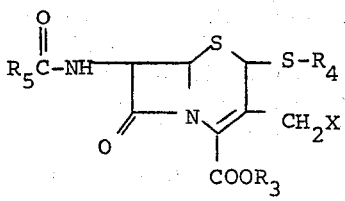

The products which are prepared by the process of this invention are useful against gram-positive bacteria, such as Staphylococcus aureus and Streptococcus pyogenes, and especially against gram-negative bacteria such as Escherichia coli and Proteus vulgaris when formulated and administered conventionally in a manner like that described in the two U.S. Patents cited above.

The following examples are illustrative of the invention and constitute preferred embodiments. All temperatures are on the centigrade scale.

EXAMPLE 1

7-Phthalimido-3-desacetoxycephalosporanic acid, t-butyl ester

A solution of 11.3 g. of 7-amino-3-desacetoxycephalosporanic acid, t-butyl ester, 6.2 g. of phthalic anhydride and 3.82 g. of triethylamine in 300 ml. of methylene chloride is stirred for 2 hours at room temperature under a nitrogen atmosphere. Acetic anhydride, 10.7 g. is then added and stirring continued for 14 hours. The solution is diluted with chloroform and washed with water, then with pH7.2 phosphate buffer. The organic solution is dried ($MgSO_4$) and then evaporated to dryness at reduced pressure. The crystalline product, 7-phthalimido-3-desacetoxycephalosporanic acid, t-butyl ester is digested with ice cold methanol before filtering. The product weighs 12.7 g., m.p. 197°–199°C.

EXAMPLE 2

7-Phthalimidocephalosporanic acid, t-butyl ester

Into a flask is placed 122 mg. (0.372 mmole) of 7-aminocephalosporanic acid, t-butyl ester, in 4 ml of methylene chloride. To this is added 58 mg. (0.387 mmole) of phthalic anhydride and 46.5 μl. (0.335 mmole) of triethylamine. This is stirred for 2 hours at room temperature. The 1 ml. (10.4 mmole) of acetic anhydride is added and the reaction mixture is stirred for 17 hours at room temperature.

The reaction is quenched with ice water and the mixture is extracted with ethyl acetate at pH 2.2 It is then washed several times with buffer (pH 7.2), dried with $MgSO_4$, filtered and concentrated to dryness giving 150 mg. (89%) of 7-phthalimidocephalosporanic acid, t-butyl ester, m.p. 177°–179°C. NMR (δ) $CDCl_3$ 7.9 (d, 4, aromatic), 5.85 (d, 1, $C_7$), 5.12 (d, 1, $C_6$), 5.08 (q, 2, —$CH_2$O—), 3.5 (s, 2, —$CH_2$S—), 2.1 (s, 3, $CH_3$), 1.6 (s, 9, t-butyl); $J_{(6-7)}$ 4.5 Hz. $J_{CH\ 0}$ 16 Hz. IR $CHCl_3$ 1795, 1728 $cm^{-1}$ carbonyl.

EXAMPLE 3

7-Phthalimido-3-desacetoxycephalosporanic acid

One gram of the product of Example 1 is treated with 25 ml. of ice cold trifluoroacetic acid and allowed to warm to 25°. After 15 minutes, the solution is evaporated at reduced pressure to deposit the product, 7-phthalimido-3-desacetoxycephalosporanic acid.

EXAMPLE 4

7-Phthalimido-4-(methylthio)-3-desacetoxy-$\Delta^2$-cephalosporanic acid t-butyl ester To a stirred solution of triphenylmethane (5 mmoles) in 20 ml. of dry dimethoxyethane at ambient temperature under argon are added 7.5 mmoles of n-butyl lithium in n-hexane. The red mixture is stirred for 15 minutes at ambient temperature. To this is added 7-phthalimido-3-desacetoxycephalosporanic acid, t-butyl ester, (5 mmoles ) in 50 ml. of dimethoxyethane. After stirring for 2 minutes methylthio mesylate (5 mmoles) in 20 ml. of dimethoxyethane is added, and the mixture is stirred for 1 hour at ambient temperaturee and then poured into ice — pH 6.6 phosphate buffer-chloroform. The chloroform extract is washed with water, then with saturated sodium chloride solution, dried ($Na_2SO_4$), and evaporated in vacuo to a residue. The residue is triturated with hexane to remove triphenylmethane, and the remaining residue is crystallized from ether to give 679 mg. of 7-phthalimido-4-(methylthio)-3-desacetoxy-$\Delta^2$-cephalosporanic acid, t-butyl ester as colorless crystals: m.p. 158°–160° (dec.); pmr (τ) ($DCCl_3$) 8.47 (9H, s, t-butyl), 8.00 (3H, broad singlet, C-3 methyl), 7.70 (3H, s, $CH_3$S—), 4.60 (1H, d, J=4.5 Hz, C-6), 4.37 (1H, i d, J = 4.5 Hz, C-7), 3.67 (1H, broad singlet, C-2), 2.17 (4H, broad singlet, aromatics); IR ($CHCl_3$1790, 1775, and 1730 (β-lactam and phthalimido carbonyls) and 1740 $cm^{-1}$ (ester C=O); mass spectrum m/e 446 ($M^+$), 399 (M—$CH_3$S), and 345 (M-t-butyl-C=O).

Thin layer chromatography of the mother liquor on silica gel in the system benzene-ethyl acetate (19:1) yields additional product (811 mg.).

EXAMPLE 5

7-Phthalimidocephalosporanic acid

By substituting one gram of the product of Example 2 in the procedure of Example 3, 7-phthalimidocephalosporanic acid is obtained.

EXAMPLE 6

7-Phthalimido-2-(methylthio)-3-desacetoxycephalosporanic acid

Into a dry flask is placed 30 mg. of 7-phthalimido-4-(methylthio)-3-desacetoxy-$\Delta^2$-cephalosporanic acid, t-butyl ester. This is cooled in an ice bath and 2 ml. of trifluoroacetic acid are added. The solution is warmed to room temperature and stirred for 20 minutes. The reaction mixture is concentrated to dryness to obtain, as a residue, 7-phthalimido-2-(methylthio)-3- desacetoxycephalosporanic acid. NMR ($\delta$) (CDCl$_3$) 7.8 (m, 4, aromatic), 5.95 (d, 1, C$_7$H), 5.57 (d, 1, C$_6$H), 4.41 (s, 1, C$_4$H), 2.28, 2.35 (s, s, 6, —CH$_3$, SCH$_3$).
IR (CHCl$_3$) 1790, 1730 cm$^{-1}$
Mass spec.: parent ion m/e 390.4.

EXAMPLE 7

7-Phthalimido-2-(methylthio)-3-desaetoxycephalosporanic acid methyl ester

Into a flask are placed 25 mg. of the product of Example 6, in 2 ml. of methylene chloride. To this is added an excess of dizomethane in an ether solution. After 5 minutes the solution is concentrated to dryness to deposit the product, 7-phthalimido-2-(methylthio)-3-desacetoxycephalosporanic acid, methyl ester, as a gum. NMR ($\delta$) (CDCl$_3$) 8.0 (m, 4, aromatic), 6.0 (d, 1, C$_7$H), 5.58 (d, 1, C$_6$H), 4.48 (s, 1, C$_4$H), 3.98 (s, 3, CH$_3$ ester), 2.3 (s, 6, CH$_3$ and —SCH$_3$).
Mass spec.: parent ion m/e 404.47.

EXAMPLE 8

7-Phthalimido-4-(methylthio)-$\Delta^2$-cephalosporanic acid, t-butyl ester

Into a dried flask are placed 193 mg. of sublimed triphenylmethane (0.785 mmole) in 8 ml. of distilled tetrahydrofuran. To this is added 0.338 ml. (0.72 mmole) of n-butyl lithium in hexane. The solution turns very deep red and is allowed to stand for 10 minutes. Then 300 mg. (0.655 mmole) of the product of Example 2 is added. The solution turns dark green and within 2 minutes 91 mg. (.720 mmole) of methylthiomethanesulfonate are added. This is stirred at room temperature 1½ hours.

The reaction mixture is poured into iced phosphate buffer, pH 6.6, and extracted with ethyl acetate; the organic layer is washed with saturated sodium chloride solution, dried, filtered and concentrated to residual rsidual gum.

The material is isolated by preparative TLC, developed with 10:1 benzene-ethyl acetate. The product 7-phthalimido-4-(methylthio)-$\Delta^2$-cephalosporanic acid, t-butyl ester, is obtained as a semi-solid (110 mg.) by extracting the fluorescent band, R$_f$ 0.26.

EXAMPLE 9

4-(Methylthio)-7-amino-3-desacetoxy-$\Delta^2$-cephalosporanic acid, t-butyl ester Into a flask filled with argon are placed 90 mg. (0.201 mmole) of 4-methylthio-7-phthalimido-3-desacetoxy-$\Delta^2$ cephalosporanic acid, t-butyl ester in 6 ml. of dry dioxane. To this is added 1 equivalent of hydrazine hydrate [0.4 ml. aliquot of a solution of 105 mg. of 100% hydrazine hydrate in 4 ml. dioxane]. This is stirred for 4 hours. The solvent is removed under reduced pressure. Then 1 equivalent (0.201 ml.) of 1N HCl in a water-dimethoxyethane solution is added and stirred for 1 hour. The reaction mixture is concentrated and redissolved in water and ethyl acetate at pH 2. The layers are separated. The aqueous phase is layered with fresh ethyl acetate and the pH adjusted to 7.7 with 0.1 N sodium hydroxide. The organic fraction is dried, filtered and concentrated. A yield of 30 mg. (71%) of 4-methylthio-7-amino-3-desacetoxy-$\Delta^2$-cephalosporanic acid, t-butyl ester is obtained.

EXAMPLE 10

7-(Phenoxyacetamido)-4-(methylthio)-3-desacetoxy-$\Delta^2$-cephalosporanic acid, t-butyl ester Into a flask are placed 31 mg. (0.1 mmole) of 7-amino-4-methylthio-3-desacetoxy-$\Delta^2$-cephalosporanic acid, t-butyl ester, in 4 ml. of methylene cloride. To this is added 13.7 $\mu$l. (0.1 mmole) of phenoxyacetyl chloride and 14 $\mu$l (0.1 mmole) triethylamine at 0°. This is stirred for 20 minutes. The reaction mixture is poured into ice water, extracted with ethyl acetate, washed pH 2.3 and again pH 7.2, and finally with saturated sodium chloride. The product is then dried, filtered and concentrated, giving 20 mg. (50%) of 7-(phenoxyacetamido)-4-(methylthio)-3-desacetoxy-$\Delta^2$-cephalosporanic acid, t-butyl ester. NMR ($\delta$) (CDCl$_3$) 7.1 (m, 6, aromatic plus NH), 6.3 (m, 1, C$_2$H), 5.6 (q, 1, C$_7$), 5.3 (d, 1, C$_6$H), 4.6 (s, 2, —CH$_2$C), 2.05, 200 (s, s, 6, —SCH$_3$—CH$_3$), 1.5 (s, 9, t-butyl).

EXAMPLE 11

7-(Phenoxyacetamido)-2-(methylthio)-3-desacetoxycephalosporanic acid

By substituting the product of Example 10 in the procedure of Example 6, 7-(phenoxyacetamido)- 2-(methylthio)-3-desacetoxycephalosporanic acid is obtained.

EXAMPLE 12

4-(Methylthio)-7-amino-$\Delta^2$-cephalosporanic acid, t-butyl ester

By substituting an equivalent amount of the product of Example 8, in the procedure of Example 9, 4-(methylthio)-7-amino-$\Delta^2$-cephalosporanic acid, t-butyl ester, is obtained.

EXAMPLE 13

7-(Phenoxyacetamido)-4-(methylthio)-$\Delta^2$-cephalosporanic acid t-butyl ester By substituting the product of Example 12 in the procedure of Example 10, 7-(phenoxyacetamido)-4-(methylthio)-$\Delta^2$-cephalosporanic acid, t-butyl ester, is obtained.

EXAMPLE 14

7-(Phenoxyacetamido)-2-(methylthio)cephalosporanic acid

By substituting the product of Example 13 in the procedure of Example 6, 7-(phenoxyacetamido)-2-(methylthio)cephalosporanic acid is obtained.

EXAMPLES 15 TO 22

By reacting the acid R$_5$COOH I (in the activated form indicated in the second column) of Table I with the 7-aminocephalosporanic acid derivative V according to the procedure of Example 10, the 7-acylamido-4-(substituted thio-$\Delta^2$-cephalosporanic acid derivative VI is obtained. By treating that product VI according to the procedure of Example 6, the 7-acylamido-2-methylthiocephalosporanic acid derivative VII in the table is obtained:

TABLE 1

| | | | (V) | | | (VI) | | | | (VII) | | | |
|---|---|---|---|---|---|---|---|---|---|---|---|---|---|
| Example | (I) $R_5CO_2H$ | Activated Form of $R_5CO_2H$ | $R_3$ | X | $R_4$ | $R_3$ | $R_4$ | $R_5$ | X | $R_3$ | $R_4$ | $R_5$ | X |
| 15 | $\phi OCH_2CO_2H$ | Acid chloride | t-Bu | $CH_3$ | $CH_3$ | t-Bu | $CH_3$ | $\phi OCH_2-$ | H | H | $CH_3$ | $\phi OCH_2-$ | $CH_3$ |
| 16 | $\phi OCH_2CO_2H$ | Acid chloride | t-Bu | OAc | $CH_3$ | t-Bu | $CH_3$ | $\phi OCH_2-$ | OAc | H | $CH_3$ | $\phi OCH_2-$ | OAc |
| 17 | $\phi CH_2CO_2H$ | Acid chloride | $Si(CH_3)_3$ | $CH_3$ | $C_2H_5$ | t-Bu | $C_2H_5$ | $\phi CH_2-$ | H | H | $C_2H_5$ | $\phi CH_2-$ | $CH_3$ |
| 18 | $\phi CH_2CO_2H$ | Acid chloride | $Si(CH_3)_3$ | OAc | $C_2H_5$ | t-Bu | $C_2H_5$ | $\phi CH_2-$ | OAc | H | $C_2H_5$ | $\phi CH_2-$ | OAc |
| 19 | (thienyl)-$CH_2CO_2H$ | Acid chloride | t-Bu | $CH_3$ | $CH_3$ | t-Bu | $CH_3$ | (thienyl)-$CH_2-$ | H | H | $CH_3$ | (thienyl)-$CH_2-$ | $CH_3$ |
| 20 | (thienyl)-$CH_2CO_2H$ | Acid chloride | t-Bu | OAc | $CH_3$ | t-Bu | $CH_3$ | (thienyl)-$CH_2-$ | OAc | H | $CH_3$ | (thienyl)-$CH_2-$ | OAc |
| 21 | $\phi CH(NH_2)CO_2H$ | Acid chloride Hydrochloride | $Si(CH_3)_2$ | $CH_3$ | $C_6H_5$ | t-Bu | $C_6H_5$ | $\phi CH(NH_2)-$ | H | H | $C_6H_5$ | $\phi CH(NH_2)-$ | $CH_3$ |
| 22 | $\phi CH(NH_2)CO_2H$ | Acid chloride Hydrochloride | $Si(CH_3)_2$ | OAc | $C_6H_5$ | t-Bu | $C_6H_5$ | $\phi CH(NH_2)-$ | OAc | H | $C_6H_5$ | $\phi CH(NH_2)-$ | OAc |

EXAMPLES 23 TO 29

By following the procedure of Example 4, but substituting the compound VIII from Table 2 for the methyl methanethiolsulfonate, the 7-phthalimido-4-(substituted thio)-3-desacetoxy-$\Delta^2$-cephalosporanic acid ester IX in the adjoining column is obtained:

EXAMPLES 30 TO 36

By following the procedure of Example 8 but substituting for methyl methanethiolsulfonate the compound VIII from Table 3, the 7-phthalimido-4-(substituted thio)-$\Delta^2$-cephalosporanic acid ester X in the adjoining column is obtained:

TABLE 2

| Example | VIII | IX ($R_4$) |
|---|---|---|
| 23 | $C_2H_5SCl$ | $C_2H_5$ |
| 24 | $ClCH_2SCl$ | $ClCH_2$ |
| 25 | $\phi SCl$ | $\phi$ |
| 26 | o-$NO_2$-$\phi SCl$ | o-$NO_2$-$\phi$ |
| 27 | $CH_3O-CH_2-S-SO_2-\phi OCH_3$ | $CH_3OCH_2$ |
| 28 | cyclohexyl-SCl | cyclohexyl |
| 29 | n-$C_4H_9SCl$ | n-$C_4H_9$ |

TABLE 3

| Example | VIII | X |
|---|---|---|

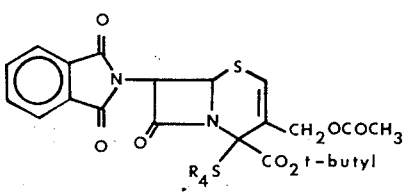

| | | $R_4$ |
|---|---|---|
| 30 | $C_2H_5SCl$ | $C_2H_5$ |
| 31 | $ClCH_2SCl$ | $ClCH_2$ |
| 32 | ⌬—SCl | φ |
| 33 | o-$NO_2$-C₆H₄-SCl | o-$NO_2$-C₆H₄- |
| 34 | $CH_3O—CH_2—S—SO_2\phi CH_3$ | $CH_3OCH_2$ |
| 35 | cyclohexyl-SCl | cyclohexyl |
| 36 | n-$C_4H_9$SCl | n-$C_4H_9$ |

EXAMPLE 37

7-Phthalamido-2-methylthio-3-desacetoxycephalosporanic acid, t-butyl ester

To 100 mg. (0.224 mmole) of the product of Example 4 in 5 ml. of dimethoxyethane and 0.25 ml. of water are added 72 mg. (0.224 mmole) of mercuric acetate. The mixture is stirred for 1 hour at room temperature under nitrogen and then stripped to dryness under vacuum. Chloroform is added, and the suspension is centrifuged. The chloroform supernatent is evaporated to a residue which is purified by tlc on silica gel in the solvent system, $CHCl_3$—EtOAc (19:1), to obtain the product 7-phthalamido-2-methylthio-3-desacetoxycephalosporanic acid, t-butyl ester, as a residue. PMR ($DCCl_2$) 8.42 (9H, s, t-butyl), 7.77 (6H, s, $SCH_3$ and C-3 methyl), 5.63 (1H, m, J=0.7 Hz, C-2 methine), 4.53 (1H, d, J=5Hz, C-6), 4.05 (1H, q, J=5Hz, J=0.7Hz, C-7), and 2.13 (4H, m, aromatics); ir ($CHCl_3$) 1796, 1775, 1740 and 1728 cm$^{-1}$.

EXAMPLE 38

7-Phthalimido-2-methylthio-3-desacetoxycephalosporanic acid

To 1 mmole of the product of Example 37 in a flask cooled in an ice-water bath are added 2 ml. of trifluoroacetic acid. The flask is stoppered, removed from the bath, and allowed to stand at room temperature for 15 minutes. The trifluoroacetic acid is removed under reduced pressure to give the product 7-phthalimido-2-methylthio- 3-desacetoxycephalosporanic acid as a residue.

EXAMPLES 39 TO 44

By treating the 7-amino-Δ²-cephalosporanic acid ester derivative XI is obtained:

TABLE 4

| Example | V | | | XI | | |
|---|---|---|---|---|---|---|
| | $R_3$ | X | $R_4$ | $R_3$ | X | $R_4$ |
| 39 | t-Bu | $CH_3$ | $CH_3$ | t-Bu | $CH_3$ | $CH_3$ |
| 40 | t-Bu | OAc | $CH_3$ | t-Bu | OAc | $CH_3$ |
| 41 | —$CH_2CCl_3$ | $CH_3$ | $C_2H_5$ | —$CH_2CCl_3$ | $CH_3$ | $C_2H_5$ |
| 42 | —$CH_2CCl_3$ | OAc | $C_2H_5$ | —$CH_2CCl_3$ | OAc | $C_2H_5$ |

TABLE 4-continued

| Example | V | | | XI | | |
|---|---|---|---|---|---|---|

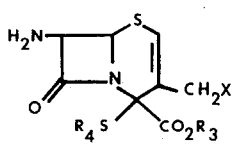
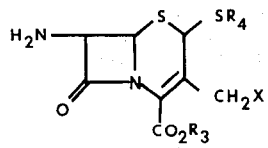

| | $R_3$ | X | $R_4$ | $R_3$ | X | $R_4$ |
|---|---|---|---|---|---|---|
| 43 | —$CH_2CCl_3$ | $CH_3$ | $C_6H_5$ | —$CH_2CCl_3$ | $CH_3$ | $C_6H_5$ |
| 44 | —$CH_2CCl_3$ | OAc | $C_6H_5$ | —$CH_2CCl_3$ | OAc | $C_6H_5$ |

What is claimed is:
1. A process for the production of a compound of the formula

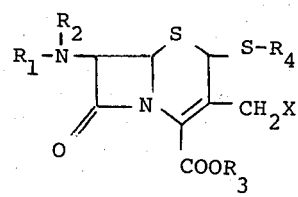

wherein $R_1$ and $R_2$ each is lower alkanoyl, benzoyl, halo-lower alkanoyl, lower alkyl-lower alkanoyl, lower alkoxy-lower alkanoyl, halobenzoyl, lower alkylbenzoyl or lower alkoxybenzoyl, or $R_1$ and $R_2$ taken together with the nitrogen form an alkyl dicarboxylic acid imide of the group consisting of maleimide, succinimide, phthalimide and naphthalene-1,2-dicarboxylic acid imide; $R_3$ is hydrogen or a protecting ester group of the group consisting of lower alkyl, lower alkoxybenzyl, halo-lower alkyl and lower alkylsilyl; $R_4$ is lower alkyl, halo-lower alkyl, lower alkoxy-lower alkyl, phenyl, halophenyl, lower alkoxyphenyl, nitrophenyl, cyanophenyl or carboalkoxyphenyl; and X is hydrogen or acetoxy,
which comprises reacting a compound of the formula

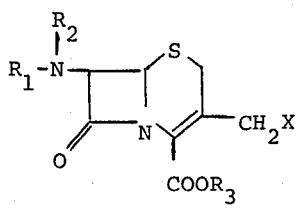

wherein $R_1$, $R_2$ and X have the meaning already defined and $R_3$ is a protecting ester group as defined above,
with a thiolating agent $R_4SY$ or $(R_4S)_2$
wherein $R_4$ has the meaning defined above and Y is halogen, lower alkoxycarbonylthio, lower alkylthio or —$SO_2$—Z wherein Z is lower alkyl or phenyl,
at a temperature in the range of about —78° to +30°C. in the presence of a strong base of the group consisting of alkali metal lower alkoxide, triphenylmethyl lithium, lithium lower alkylamide and lower metal hydride, to yield a product of the formula

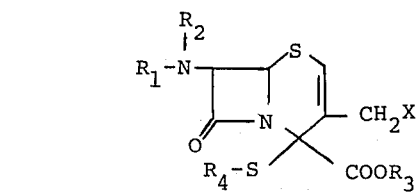

wherein $R_1$, $R_2$, $R_3$, $R_4$ and X have the meaning defined above,
and effecting the rearrangement of said product with a hydrohalic acid, trifluoroacetic acid, benzenesulfonic acid, toluenesulfonic acid, or mercury, silver or copper salt.

2. A process as in claim 1 wherein

is phthalimido.

3. A process as in claim 2 wherein $R_3$ is lower alkyl.
4. A process as in claim 3 wherein the lower alkyl group is t-butyl.
5. A process as in claim 3 wherein $R_4$ is lower alkyl and X is hydrogen.
6. A process as in claim 3 wherein $R_4$ is lower alkyl and X is acetoxy.
7. A process as in claim 4 wherein $R_4$ is methyl and X is hydrogen.
8. A process as in claim 4 wherein $R_4$ is methyl and X is acetoxy.
9. A process as in claim 1 wherein

is phthalimido, $R_3$ and $R_4$ each is lower alkyl and X is hydrogen or acetoxy.

10. A process as in claim 1 wherein the acyl group is phenylacetyl, phenoxyacetyl, thienylacetyl, α-aminophenylacetyl, α-amino-1,4-cyclohexadienylacetyl.
11. A process as in claim 9 wherein the acyl group is maleyl, $R_3$ is t-butyl and $R_4$ is methyl.
12. A compound of the formula

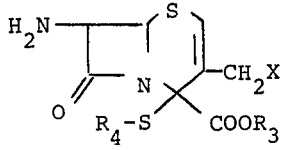

wherein $R_3$ is hydrogen or a protecting ester group of the group consisting of lower alkyl, lower alkoxybenzyl, halo-lower alkyl and lower alkylsilyl; $R_4$ is lower alkyl, halo-lower alkyl, lower alkoxy-lower alkyl, phenyl, halophenyl, lower alkoxyphenyl, nitrophenyl, cyanophenyl or carboalkoxyphenyl; and X is hydrogen or acetoxy.

13. A compound as in claim 12 wherein $R_3$ and $R_4$ each is lower alkyl and X is hydrogen or acetoxy.

14. A compound as in claim 12 wherein $R_3$ is t-butyl, $R_4$ is methyl and X is hydrogen.

15. A compound as in claim 12 wherein $R_3$ is t-butyl, $R_4$ is methyl and X is acetoxy.

16. A compound of the formula

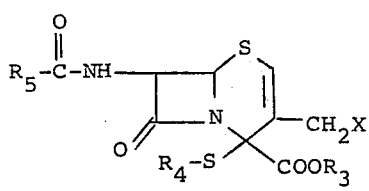

wherein $R_3$, $R_4$ and X have the same meaning as in claim 12 and $R_5$—CO is thienylacetyl, phenylacetyl, phenoxyacetyl, α-aminophenylacetyl, α-amino-1,4-cyclohexadienylacetyl.

17. A process for the production of a compound of the formula

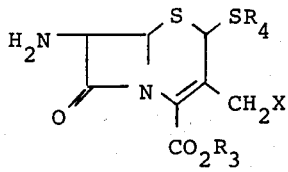

wherein $R_3$, $R_4$ and X have the same meaning as in claim 1,
which comprises effecting the rearrangement of a compound of the formula

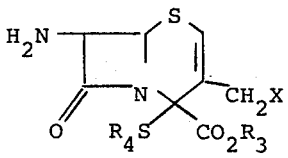

by treatment with a hydrohalic acid, trifluoroacetic acid, benzenesulfonic acid, toluenesulfonic acid, or mercury, silver or copper salt.

18. A process as in claim 17 wherein the strong acid is hydrochloric acid or trifluoroacetic acid and the metal salt is mercuric acetate, silver acetate or cupric acetate.

19. A process as in claim 18 wherein $R_3$ and $R_4$ each is lower alkyl and X is hydrogen or acetoxy.

20. A process for the production of a compound of the formula

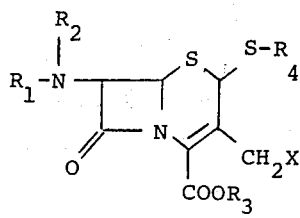

wherein $R_1$ is an acyl group $R_5$—CO— wherein $R_5$ is lower alkyl, phenyl, phenyl-lower alkyl, α-aminophenyl-lower alkyl, phenoxy-lower alkyl, lower alkoxymethyl, lower alkylthiomethyl, pyridyl-lower alkyl, thenyl, furylmethyl, ozazolylmethyl, isoxazolylmethyl, β-lower alkoxy-lower alkenyl, ($C_4$–$C_6$-cyclo-lower alkyl)-lower alkyl, α-amino-($C_4$–$C_6$-cyclo-lower alkadiene)-lower alkyl, and said aromatic and cycloaliphatic groups bearing one or two lower alkyl, lower alkoxy, halo, nitro, amino or trifluoromethyl groups; $R_2$ is hydrogen; $R_3$ is hydrogen or a protecting ester group of the group consisting of lower alkyl, lower alkoxybenzyl, halo-lower alkyl and lower akylsilyl; $R_4$ is lower alkyl, halo-lower alkyl, lower alkoxy-lower alkyl, phenyl, halophenyl, lower alkoxyphenyl, nitrophenyl, cyanophenyl or carboalkoxyphenyl; and X is hydrogen or acetoxy,
which comprises selectively cleaving with hydrazine a compound of the formula

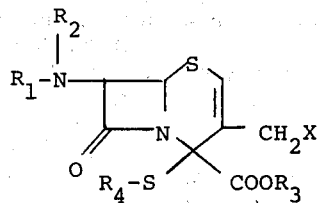

to obtain an intermediate of the formula

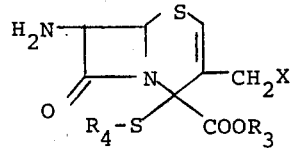

wherein $R_3$, $R_4$ and X have the meaning defined above,
acylating said intermediate with an acid halide of the formula $R_5$—CO—Y or acid anhydride of the formula $(R_5$—$CO)_2$,
wherein $R_5$ has the meaning defined above and Y is halo, azide, p-nitrophenyl or ethoxycarbonyl,
and rearrangng the acylated product with hydrohalic acid, trifluoroacetic acid, benzenesulfonic acid, toluenesulfonic acid, or mercury, silver or copper salt.

* * * * *